US008689786B2

(12) United States Patent
Schennum

(10) Patent No.: US 8,689,786 B2
(45) Date of Patent: Apr. 8, 2014

(54) AEROSOL GENERATOR

(75) Inventor: Steven Michael Schennum, Plainfield, IL (US)

(73) Assignee: British American Tobacco (Investments) Limited, London (GB)

( * ) Notice: Subject to any disclaimer, the term of this patent is extended or adjusted under 35 U.S.C. 154(b) by 617 days.

(21) Appl. No.: 12/787,259

(22) Filed: May 25, 2010

(65) Prior Publication Data

US 2011/0290249 A1 Dec. 1, 2011

(51) Int. Cl.
*A61M 15/06* (2006.01)
*A61M 11/00* (2006.01)

(52) U.S. Cl.
USPC .............................. 128/202.21; 128/200.23

(58) Field of Classification Search
USPC ............. 128/200.24, 203.12, 203.25, 202.21, 128/200.11–200.23, 203.22, 200.12, 128/200.14, 200.21, 201.21, 201.26, 128/201.28; 131/270–273; 604/57–59, 604/68–72; 222/402.24; 239/337, 338
See application file for complete search history.

(56) References Cited

U.S. PATENT DOCUMENTS

| | | | | |
|---|---|---|---|---|
| 3,062,411 | A | * | 11/1962 | De Wayne Miles .......... 222/143 |
| 3,425,414 | A | | 2/1969 | LaRoche |
| 4,171,000 | A | | 10/1979 | Uhle |
| 4,393,884 | A | | 7/1983 | Jacobs |
| 4,945,929 | A | | 8/1990 | Egilmex |
| 5,549,228 | A | * | 8/1996 | Brown .......................... 222/570 |
| 5,894,841 | A | * | 4/1999 | Voges ..................... 128/203.12 |
| 6,415,784 | B1 | * | 7/2002 | Christrup et al. ......... 128/200.23 |
| 6,494,349 | B1 | * | 12/2002 | Thompson et al. ...... 222/402.15 |
| 7,069,926 | B2 | * | 7/2006 | Skellern et al. .......... 128/200.14 |
| 2004/0000306 | A1 | | 1/2004 | Stradella |
| 2004/0094146 | A1 | * | 5/2004 | Schiewe et al. .......... 128/200.11 |
| 2005/0211733 | A1 | * | 9/2005 | Healy et al. ................ 222/402.1 |
| 2006/0018840 | A1 | * | 1/2006 | Lechuga-Ballesteros et al. ............................... 424/45 |
| 2006/0278225 | A1 | * | 12/2006 | MacMichael et al. ... 128/205.16 |

FOREIGN PATENT DOCUMENTS

| | | |
|---|---|---|
| EP | 1170061 A2 | 1/2002 |
| EP | 1237610 B1 | 5/2006 |
| GB | 2266466 A | 11/1993 |

(Continued)

OTHER PUBLICATIONS

International Preliminary Report on Patentability, mailed Nov. 2, 2012, for PCT International Application No. PCT/EP2011/057693, filed May 12, 2011.

(Continued)

*Primary Examiner* — Jackie Ho
*Assistant Examiner* — Ned T Heffner
(74) *Attorney, Agent, or Firm* — N W Poulsen

(57) ABSTRACT

An aerosol generator device comprises an elongate body with an interior passageway extending longitudinally to its mouth end. The device receives an interchangeable, pressurized canister charged with a nicotine containing liquid that is discharged in a metered dose on manual actuation of a trigger that causes a valve in the canister to open and discharge through a discharge tube. Inner and outer collar members releasably couple the canister with a bayonet action. The trigger is rotatably mounted on the body about a trigger axis spaced from and extending transversely of the longitudinal axis of the device, and has a manually depressible surface portion under a flexible cover, and a camming surface portion that drives a slidable nozzle member inwardly of the body to press the discharge tube inwardly of the canister and the valve so as to form an aerosol from the liquid released from the canister.

19 Claims, 10 Drawing Sheets

(56) References Cited

FOREIGN PATENT DOCUMENTS

| WO | WO00/12162 | A1 | 3/2000 |
|----|------------|----|--------|
| WO | WO00/53247 | A1 | 9/2000 |
| WO | WO02/100469 | A2 | 12/2002 |
| WO | WO2005/044354 | A1 | 5/2005 |
| WO | WO2009/024578 | A2 | 2/2009 |
| WO | WO2009/135729 | A1 | 11/2009 |
| WO | WO2011/015825 | | 2/2011 |

OTHER PUBLICATIONS

International Search Report and Written Opinion, mailed Aug. 25, 2011, for PCT International Application No. PCT/EP2011/057693, filed May 12, 2011.
International Search Report and Written Opinion, mailed Aug. 16, 2011, for PCT International Application No. PCT/EP2011/057603, filed May 11, 2011.
International Preliminary Report on Patentability, mailed Aug. 10, 2012, for PCT International Application No. PCT/EP2011/057603, filed May 11, 2011.
International Search Report and Written Opinion, mailed Aug. 4, 2011, for PCT International Application No. PCT/EP2011/057797, filed May 13, 2011.
International Preliminary Report on Patentability, mailed Jul. 6, 2012, for PCT International Application No. PCT/EP2011/057797, filed May 13, 2011.
Invitaton to Restrict or Pay Additonal Fees, mailed Jul. 6 2012, for PCT International Application No. PCT/EP2011/057797, filed May 13, 2011.
International Search Report and Written Opinion, mailed Aug. 17, 2011, for PCT International Application No. PCT/EP2011/057945, filed May 17, 2011.
International Preliminary Report on Patentability, mailed May 21, 2012, for PCT international Application No. PCT/EP2011/057945, filed May 17, 2011.
Non-Final Office Action, dated Dec. 10, 2012, for U.S. Appl. No. 12/787,271.
Non-Final Office Action, dated Jul. 13, 2012, for U.S. Appl. No. 12/787,258.
Final Office Action, dated Jan. 18, 2013, for U.S. Appl. No. 12/787,258.
Non-Final Office Action, dated Jun. 20, 2012, for U.S. Appl. No. 12/787,257.
Final Office Action, dated Oct. 23, 2012, for U.S. Appl. No. 12/787,257.
Non-Final Office Action, dated Dec. 4, 2013, for U.S. Appl. No. 12/787,258, filed May 25, 2010.

* cited by examiner

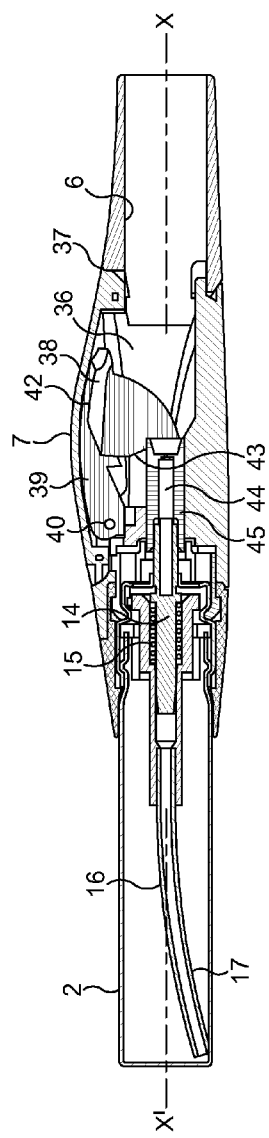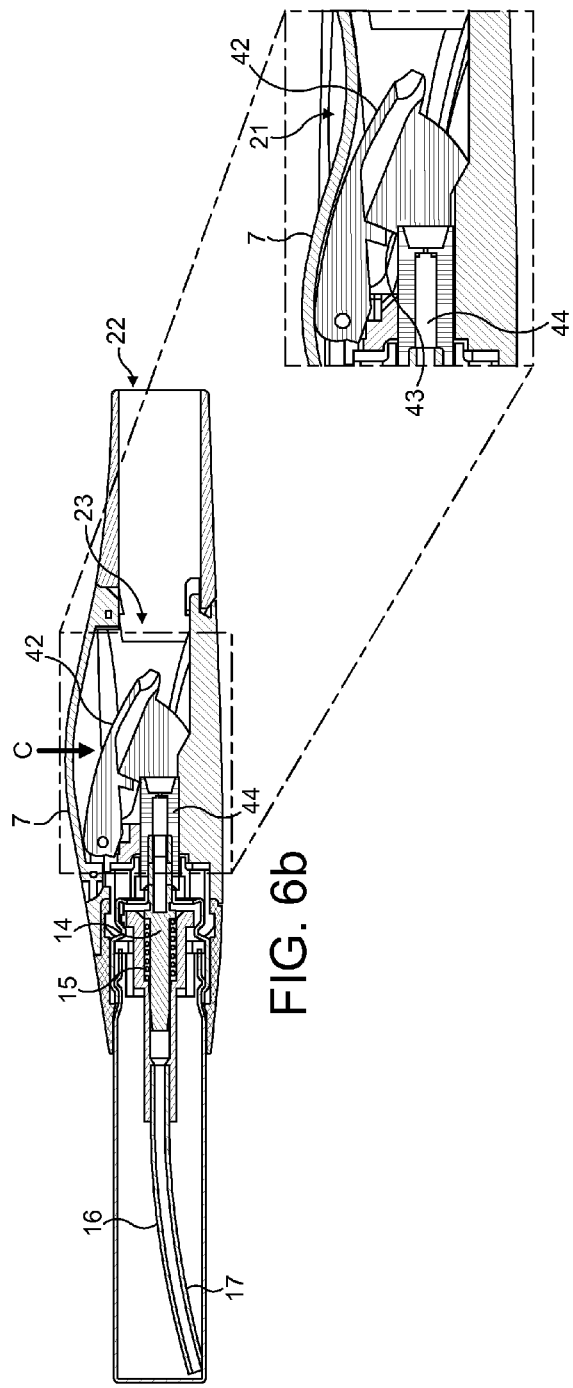

AEROSOL GENERATOR

FIELD OF THE INVENTION

This invention relates to a portable, handheld aerosol generator device which may be used to deliver aerosol to the mouth of a consumer, for example aerosol containing nicotine.

BACKGROUND

A nicotine dispensing aerosol device is disclosed in U.S. Pat. No. 4,945,929, which simulates a smoking article such as a cigarette, without having to burn tobacco.

SUMMARY OF THE INVENTION

The invention provides an improved device that can be operated manually by a consumer to generate aerosol.

An embodiment of the invention provides an aerosol generator device comprising an elongate body having a proximal mouth end, a distal end and a passageway extending longitudinally to the mouth end. A coupling is provided for releasably coupling a fluid containing pressurised canister to the body, the canister having an axial discharge tube depressible inwardly to open a valve therein to release an aerosol through the discharge tube, the canister and the passageway having a common longitudinal axis. A trigger is rotatably mounted on the body about a trigger axis spaced from and extending transversely of the longitudinal axis, the trigger having a manually depressible surface portion facing outwardly of the body, and a camming surface portion to cause the discharge tube to be pressed inwardly of the canister on depression of the surface portion inwardly of the body, to operate the valve and release the fluid from the canister through the discharge tube and through the body to the mouth end.

The trigger axis may be disposed within the body beneath its major exterior surface. The body may include a generally tubular sidewall, with the interior passageway extending from the distal end to the mouth end, and a trigger chamber extending outwardly from the interior passageway into the sidewall. The trigger can be pivotally mounted in the trigger chamber with the depressible surface portion of the trigger disposed adjacent the exterior surface of the body member.

An opening may be provided through the major exterior surface of the body into the trigger chamber, and a flexible cover may sealingly overlay the opening to be pressed inwardly to actuate the manually depressible surface portion of the trigger.

The coupling for the canister may comprise a collar arrangement to engage the canister and a collar seat on the distal end of the body, the collar arrangement being configured to sit on the collar seat and couple the canister to the distal end of the body.

The collar arrangement may include an inner collar to receive an end of the canister and be seated in the collar seat, and an outer collar to fit around the cylindrical body of the canister and over the inner collar and releasably engage with the body.

The inner collar can include interior flanges to engage crimping on the cylindrical surface of the canister to prevent axial rotation of the canister relative to the inner collar.

The inner collar may include at least one exterior lug to engage the body to prevent axial rotation of the inner collar relative to the body.

A bayonet mounting may be provided on the collar arrangement and the body, to releasably engage canister with the body.

In order that the invention may be more fully understood, embodiments thereof will now be described by way of illustrative example with reference to the accompanying drawings in which:

BRIEF DESCRIPTION OF THE DRAWINGS

FIG. 6a is a cross sectional view of the device with its trigger up;
FIG. 6b is a sectional view of the device with the trigger down, depressed in the direction of arrow C;
FIG. 6c is an enlarged view of the trigger in the configuration of FIG. 6b.

DETAILED DESCRIPTION

Figure 1:
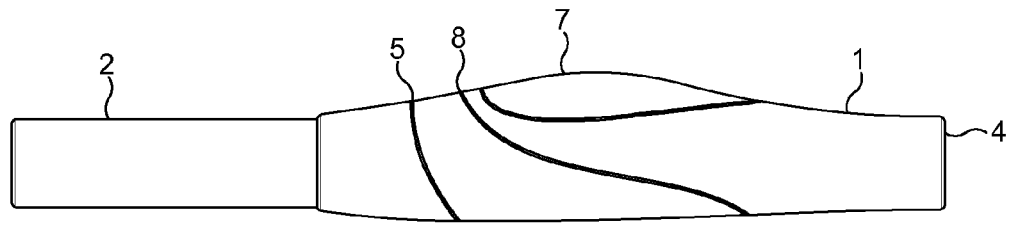
FIG. 1 is a side view of an aerosol generator device.
Figure 2:
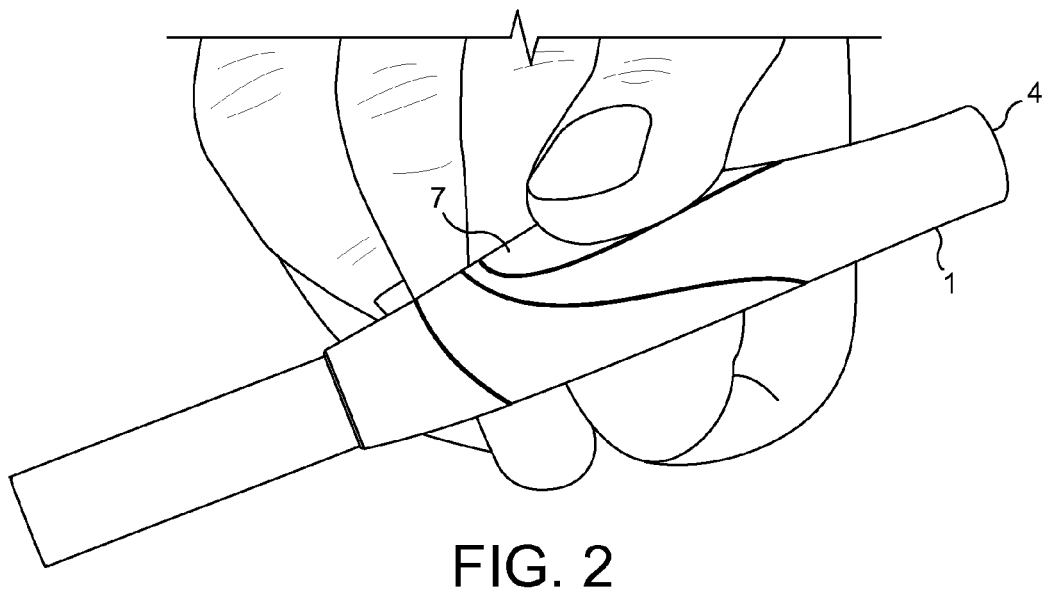
FIG. 2 is an illustration of the device of FIG. 1 held between fingers of a hand for use by a consumer.
Figure 3:
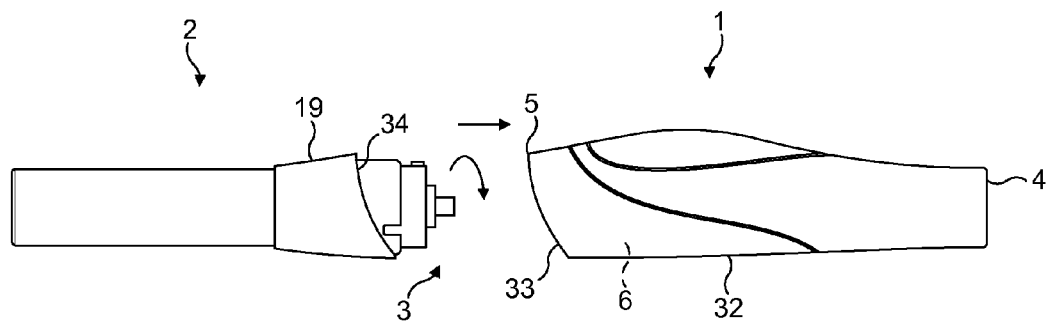
FIG. 3 illustrates a bayonet coupling to locate a pressurised canister onto the body of the device.

As shown in FIGS. 1 and 2, the device comprises an elongate, generally tubular body 1 that receives an interchangeable, vessel comprising a generally cylindrical, pressurised canister 2 that contains a liquid propellant such as but not limited to HFA 134a and a substance to be provided in an aerosol to the consumer. A bayonet mounting 3 shown in FIG. 3 allows the canister 2 to be attached and replaced on the body 1 when the contents of the canister have been consumed by the user.

The device has a proximal, mouth end 4 and a distal end 5 to which the canister 2 is attached. An interior passageway 6 extends from the distal end 5 to the mouth end 4 longitudinally of the body 1, and the cylindrical canister 2 when attached to the body 1 is located generally coaxially of the interior passageway.

The body 1 contains a trigger mechanism to be described in detail hereinafter, that enables a consumer to dispense a metered dose of an aerosol of the pressurised contents in the canister 2 by depressing a flexible cover 7 on the exterior surface 8 of the body 1, when gripping the body between their fingers as illustrated in FIG. 2. The mouth end 4 can be placed between the lips of the consumer's mouth so as to deliver the aerosol upon depression of the trigger mechanism.

Figure 5:
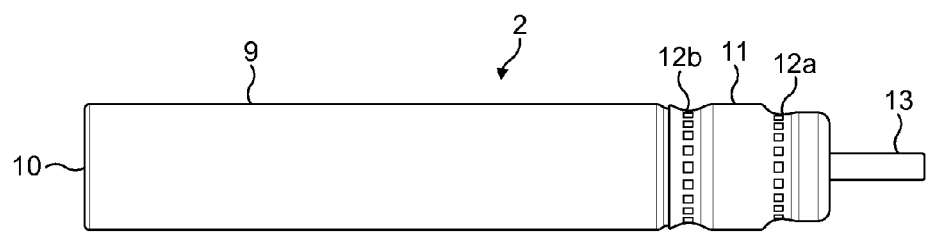
FIG. 5 is a side view of the canister for use in the device.
Figure 4:
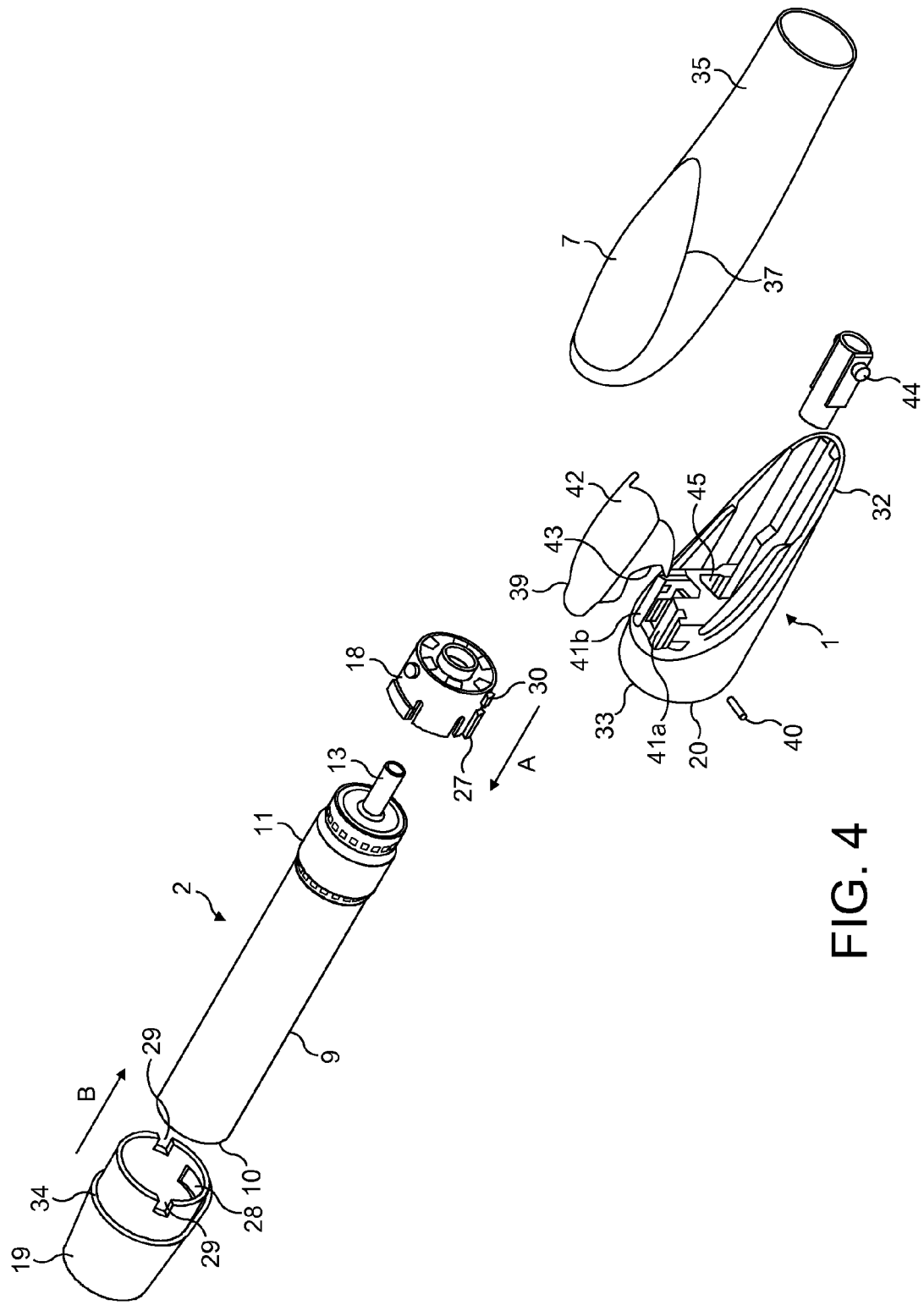
FIG. 4 is an exploded view of the components of the device.

Referring to FIGS. 4 and 5, the canister 2 comprises a generally cylindrical housing 9 with an integral base 10 at the far end of the canister and an opening at the near end that is closed by a valve cap 11 which is crimped in place over an interior gasket seal (not shown) to seal the canister closed and retain its pressurised contents therein. The crimping comprises radial crimped patterns 12a, 12b around the cylindrical surface at the near end of the canister as shown in FIG. 5, which provide a uniform, dimpled surface texture and holds the valve cap 11 onto the cylindrical housing 9 as well as holding the interior components of the valve together (not shown). A discharge tube 13 is slidably mounted along the longitudinal axis of the canister 2.

The interior structure of the canister 2 is shown in the sectional views of FIGS. 6a and 6b, mounted for operation on the body 1. The canister 2 is mounted with its longitudinal axis aligned with the longitudinal axis X-X' of the device, for dispensing aerosol from the discharge tube 13 into the passageway 6 towards the mouth end 4. A valve 14 in the canister 2 delivers a metered dose of the pressurised contents of the canister through the discharge tube 13 when it is slid axially inwardly of the canister against the force of spring 15, which urges the tube outwardly to keep the valve 14 normally closed. A supply pipe 16 feeds the pressurised contents of the canister 2 to the inlet of the valve 14 and has a curved end 17 that is disposed downwardly so that all of the contents of the canister can be fed to the valve and consumed.

The bayonet mounting that releasably holds the canister 2 on the body will now be described. Referring to FIG. 4, a collar arrangement comprising an inner collar 18 and an outer collar 19 is provided to locate the canister 2 on a collar seat 20 on the body 1.

Figure 7A:
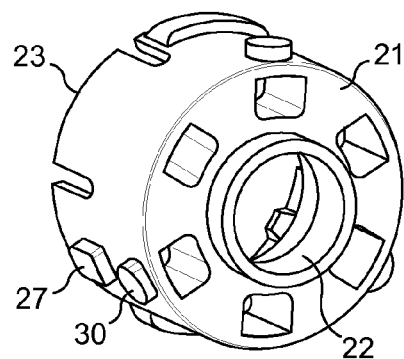
FIG. 7a is a perspective view of the inner collar from one end.
Figure 7B:
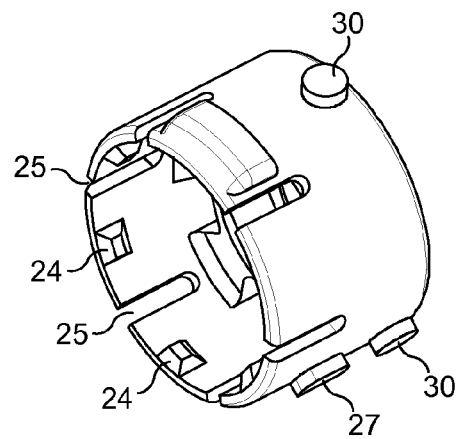
FIG. 7b is a perspective view of the inner collar from the other end.
Figure 7C:
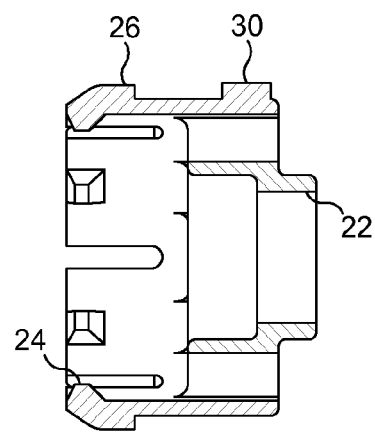
FIG. 7c is a sectional view of the inner collar.

The inner collar 18 is shown in more detail in FIGS. 7a-c, and includes an annular base 21 with a central opening 22 to be aligned with the passageway 6. A generally cylindrical sidewall 23 extends from the base 21 and includes radially disposed inner teeth 24 and slots 25. The inner and outer collars 18, 19 are conveniently integrally moulded in plastics material. In use, the collar is pushed onto the canister 2 in the direction of arrow A shown in FIG. 4 and the slots 25 permit the sidewall to flex outwardly until the teeth 24 engage in the crimping pattern 12a on the canister 2 shown in FIG. 5, to locate it in place abutting the base 21 with the discharge nozzle 13 protruding into the opening 22. The teeth 24 when engaged with the crimping 12a, prevent rotation of the canister 2 relative to the inner collar 18.

Figure 8:
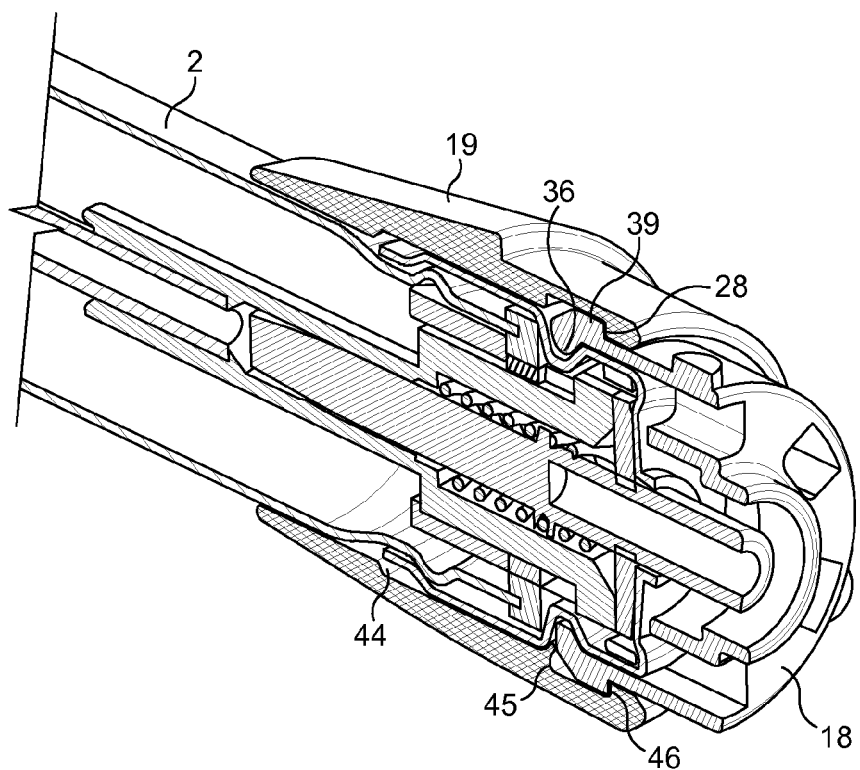
FIG. 8 is a perspective view in partial section of the collar arrangement when fitted to the canister.
Figure 9:
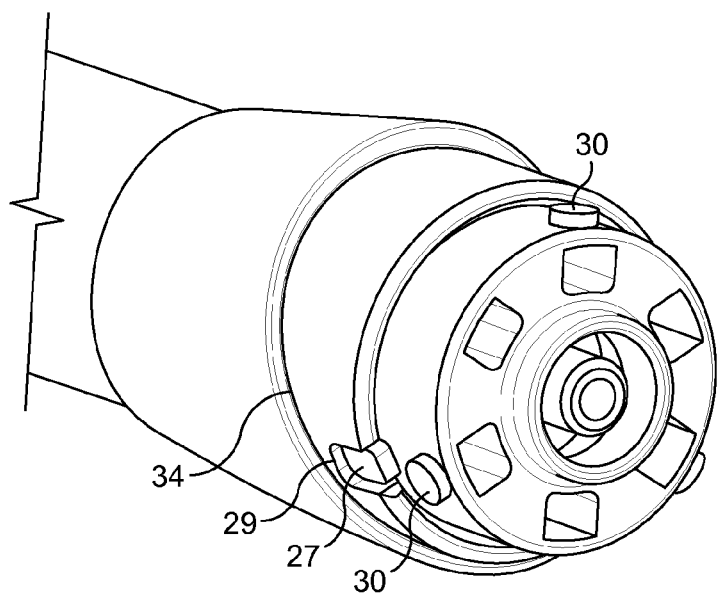
FIG. 9 is a perspective view of the inner and outer collars fitted to the canister.
Figure 10A:
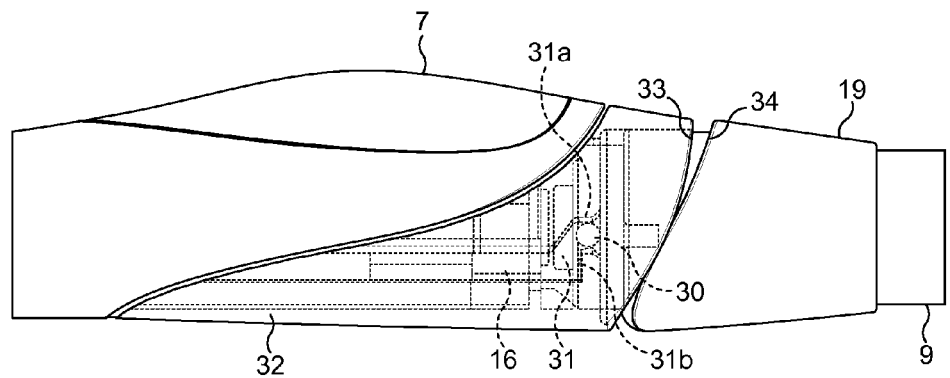
FIG. 10a illustrates the initial fitting of the canister and collar arrangement to the body member.
Figure 10B:
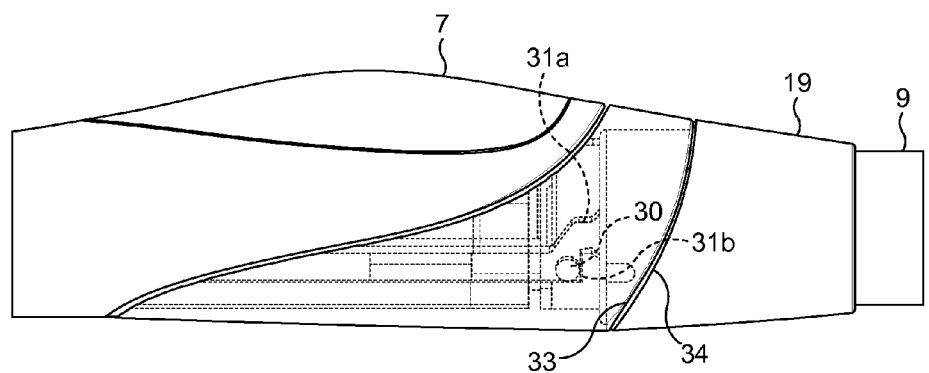
FIG. 10b illustrates the collar arrangement and canister when fitted to the body.

The outer collar 19 is fitted onto inner collar 18 by push-fitting it over the canister in the direction of arrow B shown in FIG. 4. In order to locate the outer collar 19 in place, the inner collar 18 is formed with circumferential ledge portions 26 and axially extending lugs 27 that engage an interior, circumferential lip 28 and axial grooves 29 on the outer collar, so as to locate the outer collar to prevent it rotating or moving axially relative to the inner collar and the canister 2, as illustrated in FIGS. 8 and 9. The inner collar member has bayonet lugs 30 that engage in bayonet sockets 31 in main body member 32 of the body 1 as shown in FIGS. 10a-b. The bayonet sockets include a longitudinally extending entry slot 31a that leads into a circumferentially extending retaining slot 31b. Thus, with the inner and outer collars 18, 19 attached to the canister 2, as shown in FIGS. 8 and 9, the canister 2 and collar assembly 18, 19 can be fitted onto the body 1 as shown in FIG. 10a by aligning the lugs 30 with the entry slots 31a of sockets 31, pushing the assembly axially inwardly and then rotating the assembly so that the lugs are retained in circumferentially extending slots 31b. Each of the main body member 32 and the collar 19 has peripheral ledges 33, 34 that are contiguous when the assembly is correctly aligned as shown in FIG. 10b, and assist in holding the canister 2 in place on the body 1.

Figure 11A:
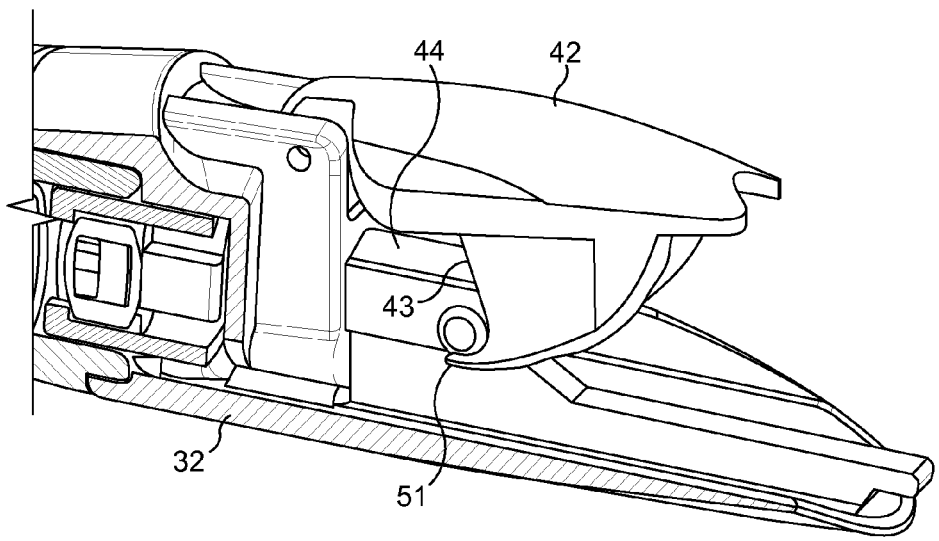
FIG. 11a is a broken away view of the body illustrating the trigger in more detail.
Figure 11B:
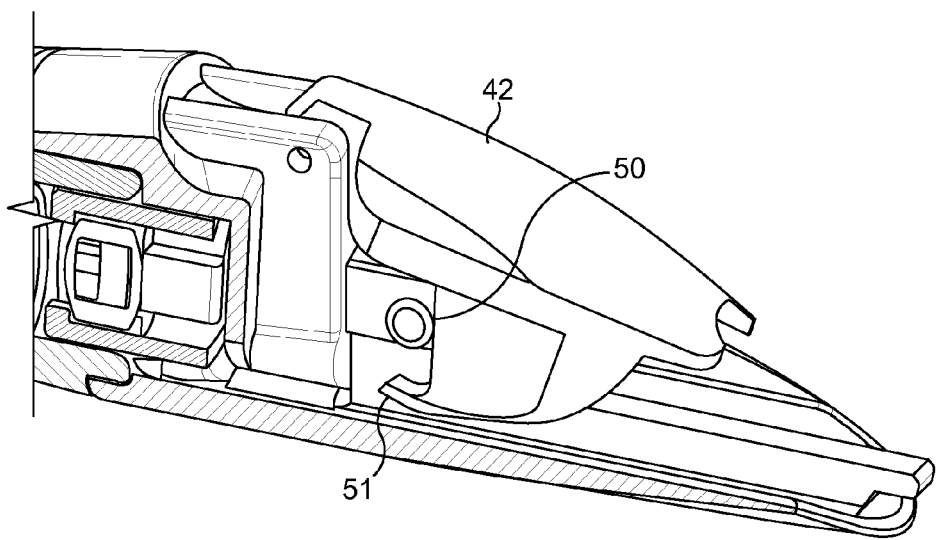
FIG. 11b illustrates the trigger and body as shown in FIG. 11A, with the trigger depressed.

Referring to FIGS. 4, 6 and 11, the body 1 includes the main body member 32 and an outlet tube 35 that can be push-fitted onto the main body member. The body members 32, 35 define a trigger chamber 36 that extends transversely from the axial passageway 6 to the exterior of the body member 1, with an opening 37 that is covered by the flexible cover 7 that is insert molded onto the body 1 so that it has a continuous, smooth, exterior major surface.

The trigger chamber 36 contains includes an interior region 38 that receives a trigger 39 in the form of a generally L-shaped lever mounted for rotation about a knurled metal pin 40 that is journalled in upstanding lugs 41a, 41b in the main body member 32 to define a trigger axis spaced from and extending transversely of the longitudinal axis X-X', within the body 1. The trigger 39 has a manually depressible surface portion 42 facing outwardly of the body, and first and second depending camming surface portions 43 to be moved longitudinally toward the canister 2 on depression of the outer facing surface portion 42 inwardly of the body in the direction of arrow C shown in FIG. 6b, by depressing the flexible cover 38. Additional textures may be added to the exterior surface of the flexible cover 38 to prompt positioning of the consumer's finger directly on the trigger for optimal lever action in use.

The camming surface portions 43 of the trigger 39 engage a tubular nozzle member 44 that is reciprocally mounted within a bore 45 in the main body member 32. As shown in more detail in FIG. 12, the nozzle member 44 includes an axial, stepped nozzle bore 46 which is arranged to fit onto the canister discharge tube 13 to receive a metered dose of the pressurised contents of the canister 2 through the discharge tube 13. The nozzle bore 46 also includes a region of restricted diameter that defines a nozzle 48 to create an aerosol of the contents discharged from the canister 2 and direct the aerosol into the passageway 6 towards the mouth of the consumer.

Figure 12A:
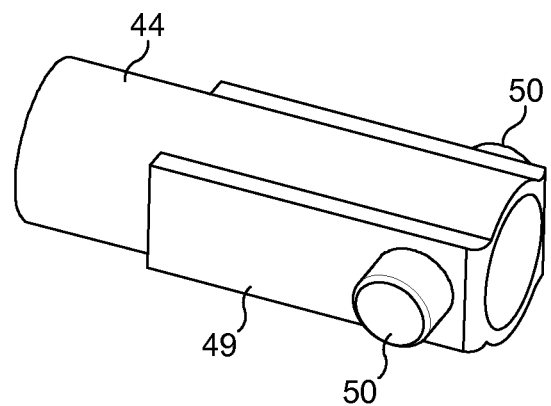
FIG. 12a is a perspective view of the nozzle member.
Figure 12B:
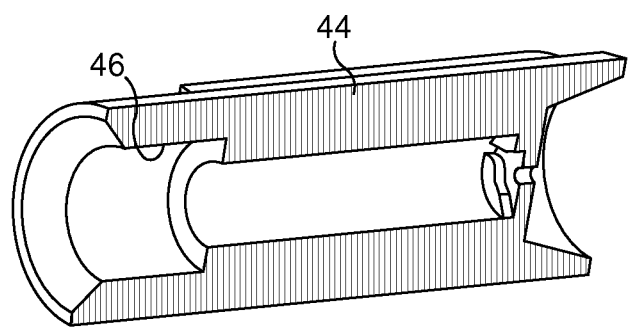
FIG. 12b is a sectional view of the nozzle member.
Figure 12C:
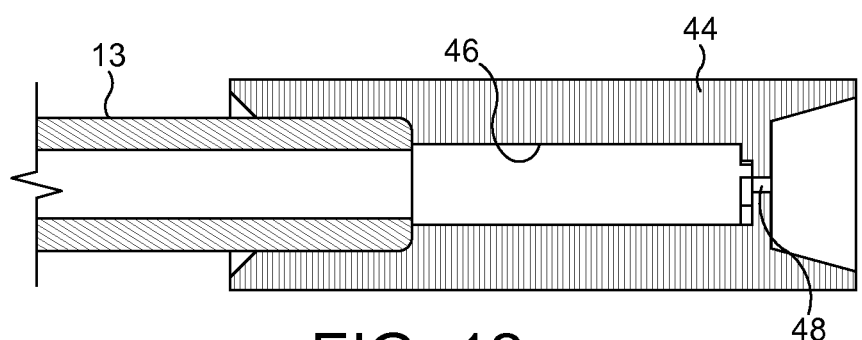
FIG. 12c is a sectional view of the nozzle member shown fitted to the discharge tube of the canister.
Figure 13:
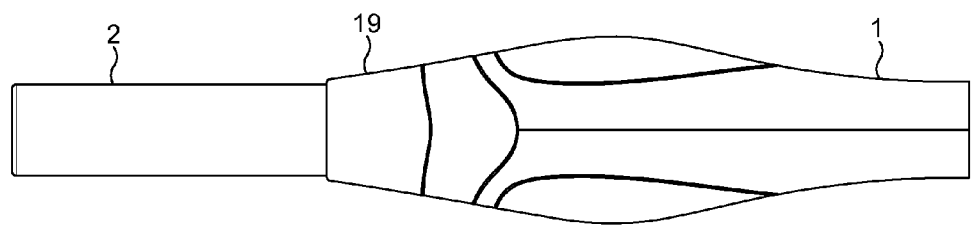
FIG. 13 is a schematic illustration of a second embodiment of the device with two triggers.
Figure 14A:
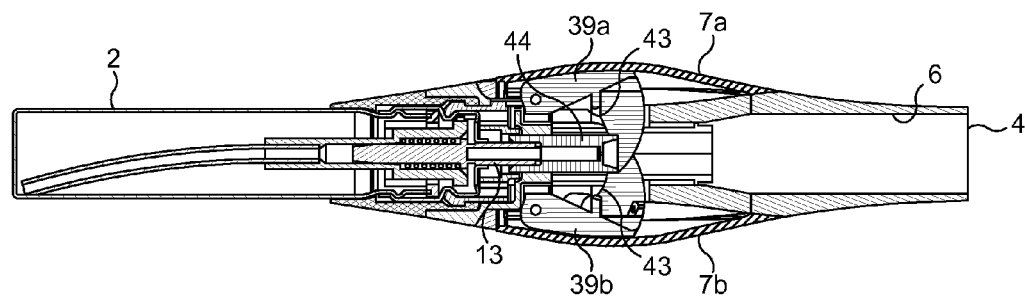
FIG. 14a is a sectional view of the device illustrated in FIG. 13.
Figure 14B:
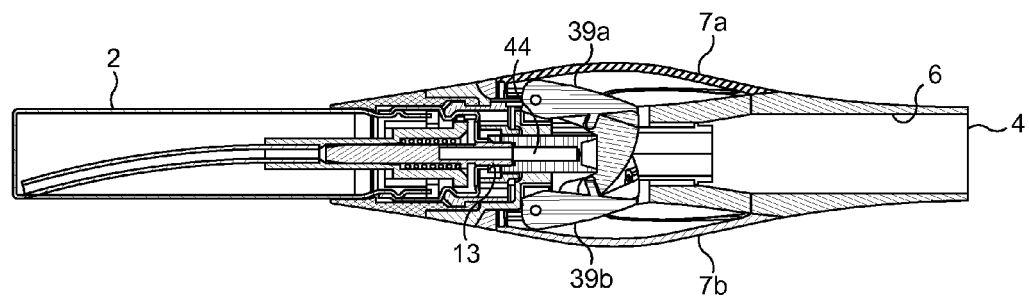
FIG. 14b corresponds to FIG. 14a, with the triggers depressed.

As shown in FIG. 12a, the nozzle member 44 includes diametrically opposed flats 49 that are received in corresponding grooves (not shown) in the main body member 32 to prevent rotation of the nozzle member when it moves back and forth. Also, the nozzle member includes first and second diametrically opposed lugs 50 that engage with the first and second camming surface portions 43 of the trigger 39 respectively. As shown in FIG. 11a, the camming surface portions include end stops 51 to limit the travel of the camming surface portions 43 along the lugs 50 so as to limit rotation of the trigger 39 which is driven against the stops 51 by the action of the spring 15 in the canister, which drives the nozzle member 44 outwardly so as to pivot the trigger upwardly against the stops 51 and flexible cover 7.

In use, a consumer places the mouth end 4 in their mouth and squeezes the cover 38 with their hand as illustrated in FIG. 2, so as to depress the lever 39 downwardly in the direction of arrow C shown in FIG. 6b. In this way, the camming surface portions 43 of the trigger urge against lugs 50 to slide the nozzle member 44 inwardly, towards the canister 2, so as to drive the discharge tube 13 inwardly of the canister against the force of its interior spring 15, to open valve 14 and release a metered dose of the contents of the canister into the discharge tube and hence into the nozzle bore 46.

As the contents discharge from the canister 2, they pass through nozzle 48 and form an aerosol, which is discharged into the interior passageway 6 as illustrated in FIG. 6b, so as to pass to the mouth of the consumer through mouth end 4.

The contents of the canister 2 may comprise a nicotine-containing liquid with or without additional flavourants, so as to simulate a smoking article such as a cigarette although it will be appreciated that other compositions may be provided within the canister 2.

From the foregoing, it will be appreciated that the canister 2 can readily be replaced when all of its contents are used up. The canister may be removed by twisting in the opposite sense to that shown in FIG. 3 to release the inner and outer collar 18, 19 from the main body member 32.

When fitting a canister, it is desirable to arrange its supply pipe 16 so that its curved end is directed generally downwardly in use to ensure that substantially all of the liquid contents can be consumed. To this end, the canister may be provided with a mark on its exterior surface that can be aligned with a corresponding mark (not shown) on the inner collar 18 disposed so that when the bayonet fitting is operated, the curved end 17 of the canister 2 is facing generally downwardly for use i.e. in the configuration illustrated in FIG. 6. An advantage of the inner and outer collar arrangement described herein is that the teeth 24 engage with the crimping to prevent rotation of the device and by providing suitable marks on the canister and the inner collar, an appropriate alignment can be effected to ensure that the curved end 17 adopts the relationship shown in FIG. 6 relative to the trigger 39, so as to face downwardly in use and enable all of the canister contents to be consumed. It is to be noted that when the inner and outer covers 18 and 19 are fitted onto the canister 2, this ensures that the curved end 17 is away from trigger 39, since the canister 2 with collar is keyed with surfaces 33 and 34.

Another embodiment of the device according to the invention as illustrated in FIGS. 13 and 14, which generally corresponds to the arrangement described hereinbefore but with two triggers 39*a*, 39*b* underlying flexible sealed cover members 7*a*, 7*b*. Each of the trigger members corresponds to the trigger 39 previously described and has camming surface portions 43 that cooperate with lugs 50 on the nozzle member 44 so that either or both of the triggers can be used to dispense a metered dose of aerosol from the canister 2. The advantage of utilising two triggers is that the force required to actuate each trigger is lower than for one alone, when used simultaneously.

Many modifications and variations fall within the scope of the invention. For example, the trigger may comprise a lever disposed exteriorly of the main body rather than under an integral cover as described hereinbefore.

Also whilst the described examples of generator device are generally cylindrical with a circular cross section, other cross sectional shapes can be used, such as rectangular or triangular.

Furthermore, although the canister is described as an interchangeable element to allow the supply of liquid to be replenished, an integral pressurised supply vessel may be provided in the device, so that the device can be used multiple times and then discarded once the liquid supply has been exhausted from the vessel. In a modification, an inlet valve may be provided to allow the supply to be replenished from an exterior, pressurised source.

The valve 14 described herein is configured to deliver a metered dose on actuation but instead, a continuous flow valve could be used such that the consumer can maintain a flow of aerosol by continuously depressing the trigger.

The mouth end can be configured differently from that shown in the Figures. For example the mouth end could be a tapered cylindrical shape with flat piece for easy positioning and orientation cue in the mouth. Also, textured or rough finishes can be applied to the exterior surface of the mouthpiece to stimulate sensation in the lips.

The supply tube of the pressurised canister may be of flexible construction and provided with a weighted end as to always assume the lowest position in the canister orientation and allow for complete consumption of the canister contents.

Inventive variations and aspects of the disclosure may include other non-limiting embodiments. For example, in one embodiment, an aerosol generator device may comprise an elongate body having a proximal mouth end, a distal end and an interior passageway extending longitudinally to the mouth end, a coupling for releasably coupling to the body, a fluid containing pressurised canister having an axial discharge tube depressible inwardly to open a valve therein to release the fluid through the discharge tube, with the canister and the passageway having a common longitudinal axis, and a trigger rotatably mounted on the body about a trigger axis spaced from and extending transversely of the longitudinal axis, the trigger having a manually depressible surface portion facing outwardly of the body, and a camming surface portion to cause the discharge tube to be pressed inwardly of the canister on depression of the surface portion inwardly of the body, to operate the valve and release the fluid from the canister through the discharge tube and through the body to the mouth end.

In one implementation, the aerosol generator device may include a tubular nozzle member slidably mounted in the body, the nozzle member having an end to abut the tube of the canister and a trigger engaging end that engages the camming surface portion of the trigger so that said inward depression of the trigger drives the nozzle member towards the distal end of the body member to drive the tube inwardly of the canister to operate the valve and release the fluid through the tube and the nozzle to provide an aerosol.

In one implementation, the body may have a major exterior surface and the trigger axis may be disposed within the body beneath said major exterior surface. In one implementation, the body may include a generally tubular sidewall, the interior passageway extending from the distal end to the mouth end, and a trigger chamber extending outwardly from the interior passageway into the sidewall, the trigger being pivotally mounted in the trigger chamber with the depressible surface portion of the trigger disposed adjacent the exterior surface of the body member. In one implementation, the aerosol generator device may include an opening through the major exterior surface of the body into the trigger chamber, and a flexible cover overlying the opening that can be pressed inwardly with the manually depressible surface portion of the trigger. In one implementation, the cover may be sealed to the body around the opening.

In one implementation, the coupling may comprise a collar arrangement to engage the canister and a collar seat on the distal end of the body, the collar arrangement being configured to sit on the collar seat and couple the canister to the distal end of the body. In one implementation, the collar arrangement may comprise an inner collar to receive an end of the canister and be seated in the collar seat, and an outer collar to fit around the cylindrical body of the canister and over the inner collar and releasably engage with the body. In one implementation, the inner collar may include interior flanges to engage crimping on the cylindrical surface of the canister to prevent axial rotation of the canister relative to the inner collar. In one implementation, the inner collar may include at least one exterior flange to engage the body to prevent axial rotation of the inner collar relative to the body. In one implementation, the aerosol generator device may include a bayonet mounting on the collar arrangement and the body, to releasably engage the canister with the body. In one implementation, the inner collar may have teeth to engage crimping on the canister.

In one implementation, the aerosol generator device may include the canister. In one implementation, the canister may be generally cylindrical and may have a valve therein configured to release a metered dose of fluid therein. In one implementation, the canister may contain a formulation including nicotine and HFA134a. In one implementation, the contents of the canister may be kept under uniform pressure by a propellant gas.

In another embodiment, an aerosol generator may comprise an elongate body having a proximal mouth end, a distal end and an interior passageway extending longitudinally to the mouth end, a coupling for releasably coupling to the body, a fluid containing pressurised canister having an axial discharge tube depressible inwardly to open a valve therein to release the fluid through the discharge tube, with the canister and the passageway having a common longitudinal axis, the collar arrangement comprising an inner collar to receive an end of the canister and be seated in the collar seat, and an outer collar to fit around the cylindrical body of the canister and over the inner collar and releasably engage with the body, and a trigger having a manually depressible surface portion facing outwardly of the body, and a camming surface portion to cause the discharge tube to be pressed inwardly of the canister on depression of the surface portion inwardly of the body, to operate the valve and release the fluid from the canister through the discharge tube and through the body to the mouth end.

In another embodiment, an aerosol generator may comprise an elongate body having a proximal mouth end, a distal end and an interior passageway extending longitudinally to the mouth end, a fluid containing pressurised gas supply vessel having a valve and a discharge tube depressible inwardly to open the valve to release fluid through the discharge tube, with the vessel and the passageway having a common longitudinal axis, and a trigger rotatably mounted on the body about a trigger axis spaced from and extending transversely of the longitudinal axis, the trigger having a manually depressible surface portion facing outwardly of the body, and a camming surface portion to cause the discharge tube to be pressed inwardly of the vessel on depression of the surface portion inwardly of the body, to operate the valve and release the fluid from the vessel through the discharge tube and through the body to the mouth end.

The invention claimed is:

1. An aerosol generator device for delivering aerosol to the mouth of a user, comprising:
    an elongate body having a proximal mouth end, a distal end, a longitudinal exterior surface extending between the proximal and distal ends, and an interior passageway extending longitudinally to the mouth end;
    a coupling to releasably couple a fluid containing pressurised canister to the body, the canister having an axial discharge tube that on inward depression opens a valve therein and releases the fluid through the discharge tube, with the canister and the passageway having a common longitudinal axis;
    a trigger rotatably mounted on the body about a trigger axis within the body that is spaced from and extending transversely of the longitudinal axis, the trigger having a manually depressible surface portion facing outwardly of the body the manually depressible surface portion being configured to be pressed inwardly of the body such that the trigger rotates inwardly towards the longitudinal axis of the body, the manually depressible surface portion being generally coextensive with the exterior surface of the body, and the trigger further including a camming surface portion configured to cause the discharge tube to be pressed inwardly of the canister on depression of the surface portion inwardly of the body, and operate the valve that releases the fluid from the canister through the discharge tube and through the body to the mouth end; and
    a tubular nozzle member slidably mounted in the body, the nozzle member having an end to abut the discharge tube of the canister and a trigger engaging end that engages the camming surface portion of the trigger, said inward depression of the trigger configured to drive the nozzle member towards the distal end of the body and the discharge tube inwardly of the canister to operate the valve and release the fluid through the discharge tube and the nozzle to provide an aerosol.

2. The aerosol generator device according to claim 1, wherein the body has a major exterior surface and the trigger axis is disposed within the body beneath said major exterior surface.

3. The aerosol generator device according to claim 2, wherein the body includes a generally tubular sidewall, the interior passageway extending from the distal end to the mouth end, and a trigger chamber extending outwardly from the interior passageway into the sidewall, the trigger being pivotally mounted in the trigger chamber with the depressible surface portion of the trigger disposed adjacent the exterior surface of the body.

4. The aerosol generator device according to claim 3, including an opening through the major exterior surface of the body into the trigger chamber, and a flexible cover overlying the opening that can be pressed inwardly with the manually depressible surface portion of the trigger.

5. The aerosol generator device according to claim 4, wherein the cover is sealed to the body around the opening.

6. The aerosol generator device according to claim 1, wherein the coupling comprises a collar arrangement configured to engage the canister and a collar seat on the distal end of the body, the collar arrangement being further configured to sit on the collar seat and couple the canister to the distal end of the body.

7. The aerosol generator device according to claim 6, wherein the collar arrangement comprises an inner collar configured to receive an end of the canister and be seated in the collar seat, and an outer collar configured to fit around the cylindrical body of the canister and over the inner collar and releasably engage with the body.

8. The aerosol generator device according to claim 6, wherein the inner collar includes interior flanges configured to engage crimping on the cylindrical surface of the canister to prevent axial rotation of the canister relative to the inner collar.

9. The aerosol generator device according to claim 6, wherein the inner collar includes at least one exterior flange configured to engage the body and prevent axial rotation of the inner collar relative to the body.

10. The aerosol generator device according to claim 6, including a bayonet mounting on the collar arrangement and the body, the mounting configured to releasably engage the canister with the body.

11. The aerosol generator device according to claim 6, wherein the inner collar comprises teeth configured to engage crimping on the canister.

12. The aerosol generator device according to claim 1, further comprising the canister coupled to the body.

13. The aerosol generator device according to claim 12, wherein the canister is generally cylindrical and comprises a valve configured to release a metered dose of the fluid.

14. The aerosol generator according to claim 12, wherein the canister comprises a formulation including nicotine and $HFA_{134}a$.

15. The aerosol generator according to claim 12, wherein contents of the canister are kept under uniform pressure by a propellant gas.

16. An aerosol generator, comprising:
an elongate body having a proximal mouth end, a distal end and an interior passageway extending longitudinally to the mouth end;
a coupling for releasably coupling to the body;
a fluid containing pressurised canister having an axial discharge tube which on inward depression opens a valve therein and releases the fluid through the discharge tube, with the canister and the passageway having a common longitudinal axis;
a collar arrangement comprising:
an inner collar configured to receive an end of the canister and be seated in the collar seat, and
an outer collar configured to fit around the cylindrical body of the canister and over the inner collar and releasably engage with the body;
a trigger having a manually depressible surface portion facing outwardly of the body and a camming surface portion configured to cause the discharge tube to be pressed inwardly of the canister on depression of the surface portion inwardly of the body, operate the valve and release the fluid from the canister through the discharge tube and through the body to the mouth end; and
a tubular nozzle member slidably mounted in the body, the nozzle member having an end to abut the discharge tube of the canister and a trigger engaging end that engages the camming surface portion of the trigger, said inward, depression of the trigger configured to drive the nozzle member towards the distal end of the body and the discharge tube inwardly of the canister to operate the valve and release the fluid through the discharge tube and the nozzle to provide an aerosol.

17. An aerosol generator, comprising:
an elongate body having a proximal mouth end, a distal end and an interior passageway extending longitudinally to the mouth end;
a fluid containing pressurised gas supply vessel having a valve and a discharge tube that on inward depression opens the valve to release fluid through the discharge tube, with the vessel and the passageway having a common longitudinal axis;
a trigger rotatably mounted on the body about a trigger axis spaced from and extending transversely of the longitudinal axis, the trigger having a manually depressible surface portion facing outwardly of the body and a camming surface portion that, on depression of the surface portion inwardly of the body, presses causes the discharge tube to be pressed inwardly of the vessel, operates the valve and releases the fluid from the vessel through the discharge tube and through the body to the mouth end, and
a tubular nozzle member slidably mounted in the body, the nozzle member having an end to abut the discharge tube of the canister and a trigger engaging end that engages the camming surface portion of the trigger, said inward, depression of the trigger configured to drive the nozzle member towards the distal end of the body and the discharge tube inwardly of the canister to operate the valve and release the fluid through the discharge tube and the nozzle to provide an aerosol.

18. The aerosol generator according to claim 17, further comprising an aerosol forming nozzle that receives the released fluid from the vessel and discharges the aerosol into the interior passageway and to the mouth end.

19. The aerosol generator according to claim 17, further comprising a fluid containing pressurised canister having an axial discharge tube that, on inward depression, opens a valve and releases the fluid through the discharge tube, with the canister and the passageway having a common longitudinal axis.

* * * * *